United States Patent [19]

Gould

[11] Patent Number: 4,682,867

[45] Date of Patent: Jul. 28, 1987

[54] APPARATUS FOR THE SELF-EXAMINATION OF THE HUMAN EYE

[76] Inventor: Herbert L. Gould, 90 Greenridge Ave., White Plains, N.Y. 10605

[21] Appl. No.: 718,873

[22] Filed: Apr. 2, 1985

[51] Int. Cl.⁴ .............................................. A61B 3/02
[52] U.S. Cl. .................................... 351/223; 351/222
[58] Field of Search ....................... 351/223, 222, 243

[56] References Cited

U.S. PATENT DOCUMENTS 3,439,978  4/1969  Moore et al. ................... 351/205 X
3,903,870  9/1975  Berndt ............................... 351/223

*Primary Examiner*—Rodney B. Bovernick
*Attorney, Agent, or Firm*—S. C. Yuter

[57] ABSTRACT

Apparatus for self-examination of the human eye comprising a pen light for generating a beam of light, a reflecting sphere for orthogonally reflecting the beam through an opaque disc having a pin hole and a cylindrical head enclosing the reflecting sphere and opaque disc. The reflecting sphere is adjustable along its axis, and functions to reflect a uniformly diffuse beam of light through the pin hole. When the pin hole is at the anterior focus of the human eye and along its pupilary axis, a viewer can see opacities in the eye.

13 Claims, 1 Drawing Figure

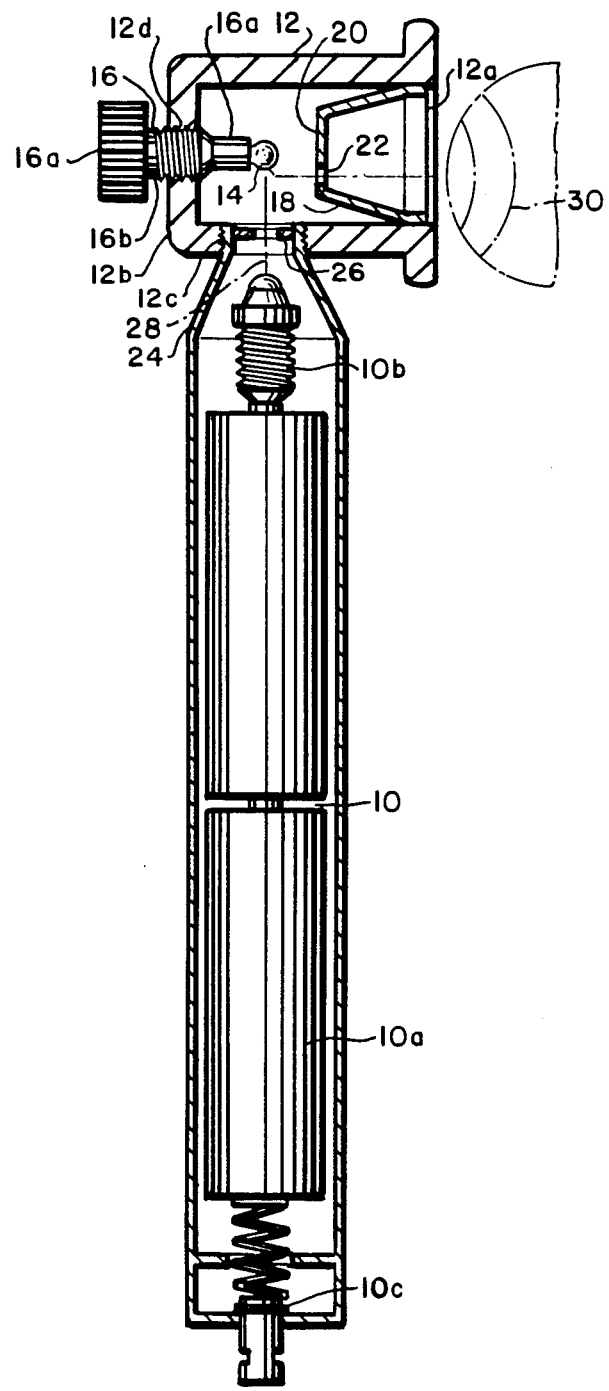

APPARATUS FOR THE SELF-EXAMINATION OF THE HUMAN EYE

BACKGROUND OF THE INVENTION

1. Field of the Invention

This invention pertains to opthalmic examining apparatus and, more particularly, to apparatus for the self-examination of the human eye which enables a patient to view various conditions of the patient's eye.

2. Description of the Related Art

Various devices have been used to enable doctors to inspect and analyze infirmities and diseases of the human eye. A serious problem with many of these devices is that eye conditions are observable only to the doctor and the patient must rely upon the skill and judgment of the doctor without any means for observing what the doctor sees.

One solution to this problem is a method and apparatus for ocular self-examination disclosed in U.S. Pat. No. 3,903,870 issued Sept. 9, 1975 to Wolf-Dieter Berndt (the "Berndt System"). The apparatus of the Berndt System is an inexpensive, hand-held device to permit a patient to perform a self-examination of the eye and thereby determine if he or she should seek professional help. The apparatus comprises a pen light with its lens bulb pointed at the inside end of a short length of optical fibre positioned along the optical axis of the lens bulb. A flexible rubber cup extending from the lens bulb end of the pen light envelopes the optical fiber. The device is held by hand in a position horizontal to the ground and pointing at the eye, with the flexible rubber cup contacting the eyeball or eyeball socket so that the outside end of the optical fibre is at the anterior focus of the eye.

If a point source of light is placed along the pupilary axis and at the anterior focus of the human eye, according to Berndt, the light rays correspond to a uniform diffuse radiator of energy which is refracted and collimated in parallel rays by the eye's optics. This phenomenon enables the viewer to see his or her own visual system when the axis of the pin hole is along the viewer's pupilary axis. That is, the viewer can see the condition of his or her eye and readily observe cataracts, scar tissue, burns, lesions, floaters and other eye conditions.

For patients who shy away from placing Berndt's flexible rubber cup in contact with the eye or the eye lashes, it is somewhat difficult to maintain the end of the optical fibre at the anterior focus distance from the eye surface while at the same time centering the emitted light on the pupilary axis of the eye. Even with the flexible rubber cup in contact with the eye holding the pen light in a horizontal position so that the emitted light is projected along the pupilary axis can be difficult.

In U.S. Pat. No. 3,787,112 issued Jan. 22, 1974 to John H. Lyons for Apparatus and Method for the Self-Examination of Certain Conditions of the Eye (the "Lyon's System"), the presence, location and nature of a cataract, retinal damage, scars and injuries can be seen by the patient. Lyon's apparatus comprises a conical housing with an eyepiece at its small end and an illuminated target panel near its larger end. An optical system is positioned adjacent its smaller end comprising negative and positive lens separated by a disc with a large pin hole (7 millimeters). Non-collimated diffused light entering the eye through the eye lens impinges upon the retina. A cataract in the eye lens causes a shadow on the retina and the viewer can perceive the outline of the cataract on the illuminated target panel. So Lyon's System, like Berndt's System, permits the self-examination of the human eye, but with a far more expensive apparatus.

BRIEF SUMMARY OF THE INVENTION

The principal object of the invention is to provide improved apparatus for the self-examination of the human eye which is easy to use and relatively inexpensive.

A more specific object of the invention is to provide a relatively inexpensive hand-held apparatus for self-examination of the eye which is easier to use than the Berndt System.

Briefly, in accordance with the invention, apparatus for the self-examination of the human eye is provided comprising a pen light to generate a beam of light and a light reflecting means to bend the light beam 90 degrees while uniformly diffusing it so that it surrounds a pin hole in an opaque disc to project a point source of uniformly diffuse light which, when placed at the anterior focus and along the pupilary axis of the human eye, is collimated by the eye's optics so that the viewer can perceive opacities such as cataracts.

An advantage of the invention is that a patient can hold the pen light vertically in a fist with the patient's thumb resting on his her cheek to comfortably and stably position the point source of light at the anterior focus and along the pupilary axis of the eye; and this can easily be done without having the patient's eye or eye lashes contact the apparatus.

A feature of the invention is the use of a polished metal sphere as the light reflecting means to uniformally diffuse the light projected from the pin hole in the opaque disc.

Other objects features and advantages of the invention will be obvious from the following Detailed Description of the Preferred Embodiment taken together with the accompanying drawing in which the sole FIGURE is a cross-sectional view of the apparatus for self-examining the human eye in accordance with the preferred embodiment of the invention.

DETAILED DESCRIPTION OF THE PREFERRED EMBODIMENT

Referring to the sole FIGURE, the improved apparatus for self-examination of the human eye generally comprises a pen light 10 connected to a cylindrical head 12 which encompasses a reflecting sphere 14 attached to an adjustable post 16 and an opaque truncated cone 18 whose truncated end comprises an opaque disc 20 having an off-centered pin hole 22.

The cylindrical head 12 has an open end 12a, a closed end 12b and a threaded aperture 12c in its side. The pen light 10 has the usual batteries 10a, lens bulb 10b and push button switch 10c. The lens bulb end of the pen light 10 has a conical portion 24 which is threadably connected to the body of the pen light 10 by means (not shown) which permits the changing of the batteries 10a and lens bulb 10b. The truncated end of the conical portion 24 screws into threaded aperture 12c of the cylinder head 12.

The adjustable post 16 has a connector portion 16a, which is attached to reflecting sphere 14, an intermediate threaded portion 16b, which is rotatably connected to the closed end 12b of cylinder head 12 in a threaded aperture 12d, and a knurled knob 16c for rotating the adjustable post 16 to move the reflecting sphere 14 along the axis of the adjustable post 16.

The inside of the opaque truncated cone 18 is black. Positioned within the truncated end opening of the conical portion 24 is a second opaque disc 26, also black, having a centered pin hole 28.

In operation, the push button switch 10c is snapped in turning on the lens bulb 10b. The lens bulb 10b projects a beam of light around the pin hole 28 of the opaque disc 26. As shown by the dashed line, a portion of the light beam having an outside diameter corresponding to the inside diameter of the pin hole 28 (1 millimeter) is projected onto the spherical surface of the reflecting sphere 14 and a portion of that beam is orthogonally reflected along the dashed line to surround the off center pin hole 22. At this point, because of the spherical reflection, the beam surrounding the pin hole 22 is uniformly diffused. A portion of that uniformly diffused beam having an outside diameter equal to the diameter of the pin hole 22 (1 millimeter) is transmitted from the pin hole 22 as a pin point source of uniformly diffused light. Then the adjustable post 16 is rotated to maximize the brightness of the circular zone of projected uniformly diffused light by optimizing the reflection by the reflecting sphere 14. The reflecting area of the reflecting sphere 14 is below the axis of the adjusting post 16 and connected reflecting sphere 14. Thus, the orthogonally reflected light impacts on the opaque disc 20 below its axis, which is why the axis of the pin hole 22 is off center.

In sum, the axis of the light beam projected by the lens bulb 10b is orthogonal to the axis of the light beam reflected by reflecting sphere 14 around the pin hole 22. And the axis of the pin hole 22 is parallel to and below the axis of the adjusting post 16 and reflecting sphere 14. And the orthogonal axes intersect at the surface of the reflecting sphere 14.

While the apparatus of the sole FIGURE is primarily used to permit a patient to view opacities and especially cataracts in the patient's eye, other eye conditions may also be perceived. Such eye conditions include, tumors, retinal burns, scar tissue, floaters, motes and lesions. Similar apparatus has also been used to detect cerebral syphilis, tabes, diabetes, prodromal chronic glaucoma, encephalitis lethargica, hypertension, ptomaine poisoning and botulism (according to Berndt).

In use by a patient, the pen light 10 is grasped in the fist of the hand on the same side as the eye to be self-examined. The thumb of that hand is then rested on the cheek or cheek bone to stabilize the apparatus in the vertical position. Then the open end 12a of the cylindrical head 12 is positioned close to the surface of the eyeball 30 and moved around until the patient sees a circular zone of light. When the opaque disc 20 is at the anterior focus and along the pupilary axis of the patient's eye, about 16 millimeters between the pin hole 22 and the surface of the eye, the eye's optics refracts and collimates the uniformly diffused light into parallel rays. Under those conditions, any opacity in the eye causes a shadow on the macular area of the retina so that the patient sees the outline of any cataract in his or her lens, or any opacity within the eye ball for example floaters.

Before the patient uses the apparatus the examining doctor, using his regular opthalmic instruments, draws an outline of the opacity, usually without showing it to the patient. Then the patient, using the apparatus sketches an outline of what he or she sees. Then the doctor shows his drawing to the patient and compares his drawing with the patient's sketch to confirm in the mind of the patient that the doctor's diagnosis is correct.

For those patients who shy away from having the apparatus contact the surface of the eyeball or even eye lashes, the support of the thumb of the hand against the cheek or cheek bone permits the pin hole of uniformly diffused light to be easily positioned at the anterior focus and along the pupilary axis long enought for the patient to make a sketch of what the patient perceives. Of course, if eye contact or eye socket contact is tolerable, then there is additional stability during the sketching period.

While the pen light 10 is shown as screwed into the side aperture 12c of the cylinder head 12, it could be friction fit or attached in any other equivalent way. Also, the penlight (10) may be disposable. Similarly, while the adjustable post 16 is shown as screwed into opening 12d of the closed end 12b of the cylindrical head 12, it could be silidably positioned along the axis of the reflecting sphere 14 to maximize the reflected light. Moreover, the cylindrical head 12 need not be cylindrical; it can have a different cross-sectional shape as long as it encompasses the opaque truncated cone 18 or an equivalent pin hole means.

What is claimed is:

1. Apparatus for the self-examination of the human eye comprising:
    (a) light source means for generating a beam of light along a given axis;
    (b) an opaque disc with an off center pin hole having an axis orthogonal to said given axis of said light source means;
    (c) sphere reflecting means positioned at the intersection of said orthogonal axes for orthogonally reflecting a beam of light from said light source means onto one side of said opaque disc and surrounding said off center pin hole; and
    (d) support means for supporting said light source means, said opaque disc and said sphere reflecting means in said orthogonal axes relationship whereby a pin point of light is transmitted from said off center pin hole to a space on the other side of said opaque disc.

2. Apparatus for the self-examination of the human eye according to claim 1 further comprising:
    (e) sphere adjusting means attached to said sphere reflecting means for adjusting the position of said sphere reflecting means along an axis parallel to the axis of said off center pin hole;
    (f) whereby a beam of light from said light source means can be centered around said off center pin hole by adjusting the position of said sphere reflecting means along said parallel axis.

3. Apparatus for the self-examination of the human eye according to claim 2 wherein:
    (g) said support means comprises a cylindrical head having the same axis as said parallel axis of said sphere adjusting means with an open end and a closed end; and
    (h) said sphere adjusting means comprises a post connected to said sphere reflecting means on the inside of said cylindrical head and having a median threaded portion passing through a matingly threaded aperture in said closed end of said cylindrical head to provide a rotatable extension extending from said closed end adapted to be rotated in order to move said sphere reflecting means along said parallel axis.

4. Apparatus for the self-examination of the human eye according to claim 3 wherein said opaque disc is mounted inside and completely closing said open end of said cylindrical head except for its off center pin hole.

5. Apparatus for the self-examination of the human eye according to claim 4 wherein the side of said cylindrical head has a threaded aperture and said light source means comprises a pen light with a lens bulb end matingly threaded into said threaded aperture of said cylindrical head.

6. Apparatus for the self-examination of the human eye according to claim 5 wherein said off center pin hole of said opaque disc is between said parallel axis and threaded side of said cylindrical head.

7. Apparatus for the self-examination of the human eye ccording to claim 6 wherein the inside of said cylindrical head from its open end to said opaque disc as well as the outside surface of said opaque disc is black.

8. Apparatus for the self-examination of the human eye according to claim 5 wherein a second opaque disc is mounted in the threaded aperture of the side of said cylindrical head and said second opaque disc has a centered pin hole having the same axis as said given axis of said light source means.

9. Apparatus for the self-examination of the human eye according to claim 4 wherein said opaque disc mounted inside said open end of said cylindrical head comprises the truncated end of a cone having its open end attached to the inside surface of said cylindrical head.

10. Apparatus for the self-examination of the human eye according to claim 9 wherein the inside surface of said cone is black.

11. Apparatus for the self-examination of the human eye according to claim 6 wherein a second opaque disc is mounted in the threaded aperture of the side of said cylindrical head and said second opaque disc has a centered pin hole having the same axis as said given axis of said light source means.

12. Apparatus for the self-examination of the human eye according to claim 11 wherein said opaque disc mounted inside said open end of said cylindrical head comprises the truncated end of a cone having its open end attached to the inside surface of said cylindrical head.

13. Apparatus for the self examination of the human eye according to claim 12 wherein the inside surface of said cone is black.

* * * * *